United States Patent [19]

Johnston et al.

[11] Patent Number: 5,760,130

[45] Date of Patent: Jun. 2, 1998

[54] AMINOSILANE/CARBODIIMIDE COUPLING OF DNA TO GLASS SUBSTRATE

[75] Inventors: Richard F. Johnston, Murphys; Mary Trounstine, San Jose, both of Calif.

[73] Assignee: Molecular Dynamics, Inc., Sunnyvale, Calif.

[21] Appl. No.: 854,989

[22] Filed: May 13, 1997

[51] Int. Cl.$^6$ ............................ C08G 63/48; C08G 63/91
[52] U.S. Cl. ...................... 525/54.2; 523/112; 604/266; 424/409; 424/422
[58] Field of Search ................... 525/54.2; 523/112; 604/266; 424/409, 422

[56] References Cited

U.S. PATENT DOCUMENTS 5,350,800  9/1994  Verhoeven et al. ............... 525/54.2

OTHER PUBLICATIONS

Guo et al., "Direct fluorescence analysis of genetic polymorphisms by hybridization with oligonucleotide arrays on glass supports", 22 *Nucleic Acids Research* 5456 (1994).

Maskos et al. "Oligonucleotide hybridisations on glass supports: a novel linker for oligonucleotide synthesis and hybridisation properties of oligonucleotides synthesised in situ", 20 *Nucleic Acids Research* 1679 (1992).

Eggers et al., "A Microchip for Quantitative Detection of Molecules Utilizing Luminescent and Radioisotope Reporter Groups", 17 *BioTechniques* 516 (1994).

Chu et al., "Derivatization of unprotected polynucleotides", 11 *Nucleic Acids Research* 6513 (1983).

*Primary Examiner*—Nathan M. Nutter
*Attorney, Agent, or Firm*—Thomas Schneck; George B.F. Yee

[57] ABSTRACT

A method for coupling DNA to a glass substrate by aminating the glass substrate with an aminosilane, reacting DNA with a carbodiimide/imidazole solution to create a 5'-phosphorimidazolide, and reacting the aminated glass substrate and phosphorimidazolide to couple the DNA to the substrate.

22 Claims, No Drawings

AMINOSILANE/CARBODIIMIDE COUPLING OF DNA TO GLASS SUBSTRATE

FIELD OF THE INVENTION

This present invention relates generally to a method for coupling DNA to a substrate. In particular, this invention relates to a method in which a glass substrate is aminated, DNA is reacted with a carbodiimide/imidazole solution to create a 5'-phosphorimidazolide, and the aminated substrate and phosphorimidazolide are reacted to couple the DNA to the substrate.

BACKGROUND ART

Attachment of oligonucleotides to glass supports has been used for both synthesis and analysis of oligonucleotides. Guo et al., 22 Nucleic Acids Research 5456 (1994), report reaction of glass slides with 3-aminopropyltrimethoxysilane to create an amino-derivatized surface, coupling of the amino groups with 1,4-phenylene diisothiocyanate to covert the amino groups to amino-reactive phenylisothiocyanate groups, and coupling of 5' amino-modified oligonucleotides to these amino-reactive groups to yield a surface bound oligonucleotide. Maskos et al., 20 Nucleic Acids Research 1679 (1992), describe preparation of a glass substrate for synthesis of oligonucleotides. The substrate is first treated with 3-glycidoxypropyltrimethoxysilane, which binds to the glass. The epoxide group is cleaved with a diol or water under acidic conditions, leaving an alcohol target for in situ oligonucleotide synthesis. Eggers et al., 17 BioTechniques 516 (1994), report a similar technique for binding oligonucleotides to glass substrates.

Verhoeven et al., U.S. Pat. No. 5,350,800, teach a method for attaching a biomolecule to an aminated solid surface by reacting carboxyl groups of the biomolecule with a carbodiimide, and then reacting the carbodiimide activated carboxyl groups with the aminated solid surface to bind the biomolecule to the surface.

Chu et al, 11 Nucleic Acids Research 6513 (1983), describe creation of a 5'-phosphorimidazolide by treatment of an oligonucleotide with a carbodiimide in imidazole buffer. Chu et al. suggest that the 5'-phosphorimidazolide can be isolated and treated with an excess of an amine to obtain a 5'-phosphoramidate, creating a method suitable to attachment of oligonucleotides (including DNA and RNA) to small molecules such as ethylenediamine, polymers such as polylysine, or proteins.

SUMMARY OF THE INVENTION

It is a primary object of the present invention to provide a reliable and robust method for coupling DNA including oligonucleotides to a glass substrate.

Another object of the present invention is to provide a method for creating a stable glass substrate to which DNA may be coupled.

A further object of the present invention is to provide a method for activating DNA for coupling to a glass substrate which is simple, in which the activated DNA is stable, and in which the activated DNA couples efficiently with the glass substrate.

Briefly, the preferred embodiment of the present invention is a method for coupling DNA to a glass substrate by aminating the glass substrate with an aminosilane, reacting DNA with a carbodiimide/imidazole solution to create a 5'-phosphorimidazolide, and reacting the aminated glass substrate and phosphorimidazolide to couple the DNA to the substrate.

BEST MODE FOR CARRYING OUT THE INVENTION

This invention provides a reliable and robust method for coupling DNA (or oligonucleotides) to a glass substrate, in which a stable glass surface is created, DNA activation is simple, the activated DNA is stable, and the activated DNA couples efficiently with the glass substrate. A high binding efficiency of DNA to the substrate is achieved. The resulting process is particularly useful for binding multiple DNA fragments to create a test array on a slide.

In the preferred embodiment of the present invention, DNA or oligos in aqueous solution are deposited into an aminated slide by micropipette, crosslinked to the slide using UV light, activated by treating the DNA with a carbodiimide/imidazole solution, and attached to the slide by reacting the activated DNA with the aminated slide. This process allows creation of an array of DNA on the slide. After the DNA is bound to the slide, the DNA may be screened with techniques such as scanning of fluorescence from labeled DNA hybridized with the DNA strands bound to the slide. Slides used in the present invention typically have a size of 1 by 3 inches, and are composed of white soda lime glass. On such a slide, an array of 10,000 DNA spots can be created by depositing a grid of spots. The deposition is achieved by automated micropipetting of an aqueous DNA solution. In the preferred embodiment, each spot of DNA has a diameter of less than 150 gm, with the center to center spacing of the spots approximately 500 gm.

The present invention is described with regard to binding of DNA to a glass slide, by attaching an amine group to the surface of the glass slide and binding DNA to the amine group. However, substrates of materials other than glass may also be used by binding an amine to the substrate surface. U.S. Pat. No. 5,350,800 discusses amination of other substrates, and such techniques are applicable to the present invention.

Glass slides used in the present invention are first cleaned. The slides are immersed in 1M KOH in water for two hours at 50° C. The slides are then rinsed with deionized water, and immersed in 0.1M HCl in water for 30 minutes. Following the acid soak, the slides are again rinsed with deionized water and then dried. After cleaning, the slides are aminated. This is accomplished by immersion of the slides in 0.05M HCl containing 2% by volume 3-aminopropyltrimethoxysilane (Aldrich Chemical) for two hours at 50° C. with gentle agitation. The slides are then washed six times for ten minutes each in 0.05M HCl, followed by two washes for 10 minutes with deionized water. After washing, the slides are cured at 100° C. for eighteen hours. The surface is believed to become aminated by the following process:

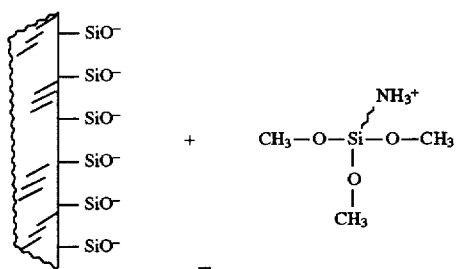

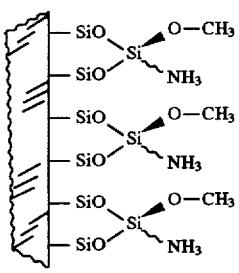

This reaction provides primary amine groups to which the DNA is subsequently attached. Amination of the surface is referred to herein as "activation" of the surface. We have found that the activated slides are very stable, and may be stored for extended periods of time—6 months at room temperature in a desiccator or inert atmosphere. Other aminosilanes in addition to the 3-aminopropyltrimethoxysilane HLD4 :024 .APL A (e.g. 3-aminopropyltriethoxysilane) are also suitable for activating the slide surface.

After a slide is aminated (activated), an array of DNA may be deposited onto the slide. The DNA is suspended in 0.1M imidazole (pH 6–10), 10 mM Tris pH 7.5, and 2 mM EDTA, typically at concentrations in the range of 1.0 mM to 5.0 μm. We have found that, after deposition of the DNA solution onto the slide, attachment of the DNA to the slide is improved by immediately subjecting the array to a pulse of 254 nm light of 500 millijoules. We believe that the effect of this UV pulse is to temporarily crosslink the DNA, reducing the likelihood that the DNA will lift off during processing from the spot where it was deposited.

Once the DNA has been deposited and crosslinked, the DNA is treated with a solution of carbodiimide in imidazole buffer. The carbodiimide used is preferably a water soluble carbodiimide of the structure $R_1N=C=NR_2$, where $R_1$ can be an alkyl or cycloalkyl group and $R_2$ can be an alkyl amine or cycloalkyl amine group, such as 1-ethyl-3-(3-dimethylaminopropyl) carbodiimide. In the preferred embodiment, an aqueous solution of 0.1M 1-ethyl-3-(3-dimethylaminopropyl) carbodiimide and 3.0M imidazole pH 6 solution is created. In the preferred embodiment, the glass slide holding the DNA spot array is placed in a sealed chamber. The aqueous carbodiimide/imidazole solution is vaporized at a temperature of approximately 500° C. The slide is maintained in the chamber for 14 hours.

The carbodiimide induced coupling of DNA to imidazole and the binding of activated DNA to the aminated substrate are believed to involve the following reactions:

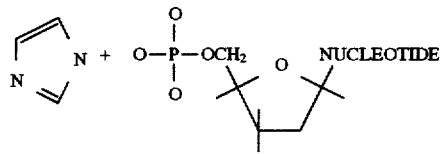

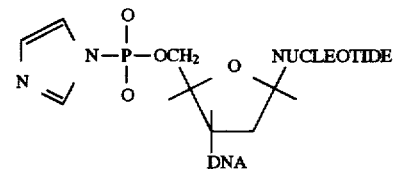

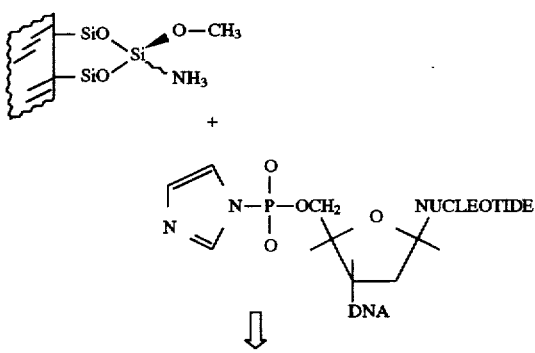

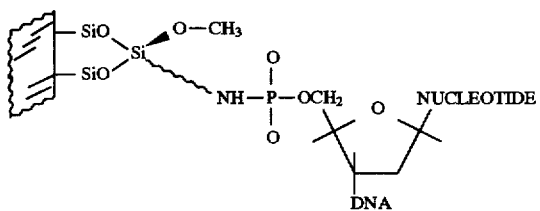

In the first reaction (1), the imidazole is attached to the 5' phosphate group of DNA. The 5'-phosphorimidazolide then reacts with the aminated substrate, attaching the DNA to the substrate. We have found that the carbodiimide vapor technique described above attaches DNA to the substrate with 90% to 100% efficiency. However, the DNA can also be activated in a carbodiimide/imidazole bath. An aqueous 0.1M 1-ethyl-3-(3-dimethylaminopropyl) carbodiimide/3 M imidazole solution is used. The slides containing crosslinked DNA spots are placed in a container with the DNA side up. Two to four ml of the solution is placed on a slide for 20 seconds. The slides are then cured in a humid chamber (70% humidity) for 50° C. for one hour. The attachment efficiency using this technique is approximately 10%.

These two techniques for attaching DNA to the aminated substrate (carbodiimide vapor and/or carbodiimide placed on the slide, in both cases applied after DNA spots are deposited on the slide) involve concomitant reaction of the DNA with the imidazole and reaction of the activated DNA with the aminated substrate. Alternatively, the DNA may be pretreated with the carbodiimide/imidazole and then brought into contact with the aminated support.

Cleanliness of reagents used in this process is critical. Reagents, including water, may not be stored in plastic containers. The substrate cannot be handled by hands or with gloves during any of the treatment, and the slides must be kept dust free.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

We claim:

1. A method for attaching DNA including oligonucleotides to a substrate surface comprising the steps of:

(a) aminating the substrate surface;

(b) forming an aqueous DNA suspension in a solution of imidazole and depositing the DNA suspension on the aminated substrate; and (c) reacting the suspension-bearing substrate with a vaporized aqueous solution containing a combination of carbodiimide and imidazole.

2. The method of claim 1 wherein the surface is glass.

3. The method of claim 1 wherein the step of forming a DNA suspension includes suspending DNA in a solution containing 0.1 M imidazole.

4. The method of claim 3 wherein the 0.1M imidazole has a pH in the range 6–10.

5. The method of claim 1 wherein the combination of carbodiimide and imidazole is prepared by combining 3M imidazole at a pH of 6 with 0.1M carbodiimide.

6. The method of claim 1 further comprising, prior to the step of reacting, a step of crosslinking the DNA by subjecting the DNA to flash photolysis with ultraviolet light.

7. The method of claim 1 wherein the substrate surface is aminated with an aminosilane compound.

8. The method of claim 7 wherein the aminosilane compound is 3-aminopropyltrimethoxysilane.

9. The method of claim 7 further comprising, prior to the step of reacting, a step of crosslinking the DNA by subjecting the DNA to flash photolysis with ultraviolet light.

10. The method of claim 7 wherein the step of forming a DNA suspension includes suspending DNA in a solution containing 0.1 M imidazole.

11. The method of claim 10 wherein the carbodiimide has the structure $R_1N=C=NR_2$, where $R_1$ is an alkyl or cycloalkyl amine group and $R_2$ is an alkylamine or cylcoalkylamine group.

12. The method of claim 11 wherein the combination of carbodiimide and imidazole is prepared by combining 3M imidazole at a pH of 6 with 0.1M carbodiimide.

13. The method of claim 11 further comprising, prior to the step of reacting, a step of crosslinking the DNA by subjecting the DNA to flash photolysis with ultraviolet light.

14. The method of claim 1 wherein the carbodiimide has the structure $R_1N=C=NR_2$, where $R_1$ is an alkyl or cycloalkyl amine group and $R_2$ is an alkylamine or cylcoalkylamine group.

15. The method of claim 14 wherein the carbodiimide is 1-ethyl-3-(3-dimethylaminopropyl) carbodiimide.

16. The method of claim 15 wherein the combination of carbodiimide and imidazole is prepared by combining 3M imidazole at a pH of 6 with 0.1M carbodiimide.

17. The method of claim 14 further comprising, prior to the step of reacting, a step of crosslinking the DNA by subjecting the DNA to flash photolysis with ultraviolet light.

18. A method for attaching DNA including oligonucleotides to a substrate surface, comprising the steps of:

(a) aminating the substrate surface;

(b) activating the DNA by immersing the DNA in a bath comprising a combination of a carbodiimide and imidazole; and (c) reacting the activated DNA with the aminated surface to attach the DNA to the substrate surface.

19. The method of claim 18 further comprising the steps of:

(a) depositing the DNA in aqueous solution onto the substrate; and (b) then crosslinking the DNA by subjecting the DNA to flash photolysis with ultraviolet light.

20. The method of claim 19 wherein the substrate surface is aminated with an aminosilane compound.

21. The method of claim 20 wherein the aminosilane compound is 3-aminopropyltrimethoxysilane and the carbodiimide has the structure $R_1N=C=NR_2$, where $R_1$ is an alkyl or cycloalkyl amine group and R2 is an alkylamine or cylcoalkylamine group.

22. The method of claim 21 wherein the combination of carbodiimide and imidazole is prepared by combining 3M imidazole at a pH of 6 with 0.1M carbodiimide.

* * * * *